United States Patent [19]

Grimshaw et al.

[11] Patent Number: 4,994,275
[45] Date of Patent: Feb. 19, 1991

[54] VETERINARY DEVICES

[75] Inventors: William T. R. Grimshaw; Andrew J. Weatherley, both of New York, N.Y.

[73] Assignee: Pfizer Inc., New York, N.Y.

[21] Appl. No.: 371,479

[22] Filed: Jun. 26, 1989

[30] Foreign Application Priority Data

Jul. 5, 1988 [GB] United Kingdom ............... 8815968

[51] Int. Cl.$^5$ ............................................. A23K 1/18
[52] U.S. Cl. ................................. 424/438; 424/424; 424/426; 424/436
[58] Field of Search ............... 424/424, 426, 438, 473, 424/436; 252/52 A; 206/407, 416, 226

[56] References Cited

U.S. PATENT DOCUMENTS

| | | | |
|---|---|---|---|
| 3,926,188 | 12/1975 | Baker et al. | 128/260 |
| 4,144,317 | 3/1979 | Higuchi et al. | 424/21 |
| 4,217,898 | 8/1980 | Theeuwes | 128/260 |
| 4,228,149 | 10/1980 | Brewer et al. | 424/14 |
| 4,402,693 | 9/1983 | Roseman | 604/890 |
| 4,505,711 | 3/1985 | Lucas | 604/892 |
| 4,601,893 | 7/1986 | Cardinal | 424/15 |
| 4,792,448 | 12/1988 | Ranade | 424/438 |
| 4,861,596 | 8/1989 | Curtiss | 424/438 |
| 4,867,980 | 9/1989 | Edwards | 424/438 |

FOREIGN PATENT DOCUMENTS

| | | |
|---|---|---|
| 10987 | 5/1980 | European Pat. Off. . |
| 21758 | 1/1981 | European Pat. Off. . |
| 153070 | 8/1985 | European Pat. Off. . |
| 1318259 | 8/1970 | United Kingdom . |

*Primary Examiner*—Merrell C. Cashion, Jr.
*Assistant Examiner*—D. Gabrielle Phelan
*Attorney, Agent, or Firm*—Peter C. Richardson; J. Trevor Lumb; A. Dean Olson

[57] ABSTRACT

Device for oral administration of a medicament to a ruminant animal comprises a rilaminate sheet (1) containing the medicament rolled into a tube retained in the rolled configuration by a film (3) of material which disintegrates in the rumen to allow unrolling of the sheet. The tube ends are closed by plugs (2) which keep the tube closed during passage of the device through the oesophagus.

6 Claims, 1 Drawing Sheet

VETERINARY DEVICES

BACKGROUND OF THE INVENTION

This invention relates to devices for administration of veterinary preparations for ruminant animals.

Ruminant animals, particularly cattle and sheep, form an important group of animals which require periodic administration of veterinary medicines for the treatment and alleviation of various conditions. For example, it is often desirable to treat such animals, either therapeutically or prophylactically, with mineral or vitamin supplements, antibiotics, systemic insecticides, detergents for the relief of cattle bloat, and/or anthelmintics or other anti-parasitic agents. The repeated administration of such veterinary medicines to animals at frequent time intervals is expensive and inconvenient. There is therefore much need for a dosing system to be devised which would efficiently supply the veterinary medicine during prolonged periods of time after administration of a single preparation.

British Pat. No. 1318259 describes a number of devices for retaining slow release veterinary medicament formulations in the rumen over an extended period of time, thereby achieving the desired result. This prolonged retention in the rumen is obtained by the devices having a relatively narrow first configuration which allows the devices to be administered per os to the ruminant, and a relatively broad second configuration which the devices assume or are caused to assume in the rumen thereby hindering or preventing their passage out of the rumen. A typical example of such a device specifically described in said Pat. No. 1318259 is a plastic cylindrical capsule containing a detergent for the control of bloat in cattle. The capsule is 150 mm long and 30 mm wide (thereby allowing per os administration), and consisting of two half-cylinders hinged along one edge. The hinges are made from rubber and are biased so that the two half-cylinders spring apart in the rumen and thus become too wide to pass out through the rumen or to be regurgitated through the oesophagus. Each half-cylinder contains a gel of ethyl cellulose containing the desired anti-bloat agent which is leached from the gel by the rumen fluids over an extended period of time. The hinges are constructed so that under the rumen conditions they pull away from the half-cylinders after effective release of the agent thereby facilitating regurgitation of the fragmented device.

Other veterinary devices intended to achieve the same result are described in European patent applications Nos. 10987A and 21758A. These devices may comprise a flexible carrier sheet rolled into an open-ended tube-like configuration which is generally cylindrical, the sheet being constrained in that configuration by strips of gummed paper or similar means which are released when the preparation enters the rumen and becomes immersed in the rumen fluids. Typical dimensions of the cylinder formed by the sheet in its rolled-up condition are 3 cm diameter and 10 cm length. The preparation in its cylindrical state may be administered to the animal by means of a balling gun and enters the rumen through the oseophagus. In the rumen the constraining means become released and the sheet unrolls to an opened, relatively broad configuration in which it remains in the rumen and cannot escape. The sheet contains a medicament which is discharged into the rumen fluid over a period of time and the sheet is adapted to discharge the medicament at a predetermined rate. One such sheet is described in European patent application No. 0153070A and comprises a plastics core layer providing a matrix containing the medicament coated on its major surfaces with an inert plastics coating to form a trilaminate, the trilaminate having a pattern of perforations through which the medicament is discharged in the rumen. The rate of discharge of the medicament is determined primarily by the number and size of the perforations.

It has been found that such open-ended rolled-up sheet devices, while operating efficiently after entering the rumen, may become stuck in the oesophagus when administered to ruminants, particularly small calves, and are not ejected by the natural regurgitation action of the animal. The constraining means may then be released in the oesophagus and the sheet become unrolled so that it becomes impacted and cannot be removed. Permanent obstruction of the oesophagus in this way has serious consequences for the animal and is normally fatal.

Attempts have been made to avoid this problem by providing increased lubrication for the preparation, for example by coating it with corn oil or polyethylene glycol wax to ease its passage into the rumen. However, it has been found that impaction of the preparation in the oesophagus still occurs in a significant proportion of the animals treated.

SUMMARY OF THE INVENTION

The present invention is intended to provide a pharmaceutical device which avoids or alleviates this problem. According to one aspect of the invention, a device for oral administration of a medicament to a ruminant animal comprises a sheet of flexible material containing the medicament and capable of slow release of the medicament within the rumen, the sheet being rolled or folded into a tube configuration and constrained in that configuration by means releasable on contact with rumen fluids so that the sheet may unroll or unfold after insertion in the rumen and remain therein, the ends of the tube formed by the sheet being provided with closing means allowing said unrolling or unfolding of the sheet in the rumen, said closing means keeping the tube ends closed during administration of the device and passage thereof into the rumen.

It has been found that when the ends of the tube are closed as the device passes through the oesophagus there is little or no risk of the device becoming impacted therein. The device in its rolled or folded condition normally passes through into the rumen, but if it fails to do so the device is regurgitated from the oseophagus spontaneously by the animal.

The tube ends should be closed by means which are retained by the device sufficiently firmly to prevent the closing means being released from the device before it enters the rumen, but which do not interfere with the unrolling or unfolding once the constraining means is released. The closing means can comprise of plugs extending into the ends of the tube and engaging its inner surface, preferably by a simple interference fit which is sufficiently tight to retain the plugs in place when the device is administered and passes through the oesophagus. The plugs can be made of any biologically acceptable material and can be of plastics material such as polyethylene.

In one embodiment, the closing means comprises such plugs having a cylindrical body portion provided with at least one radially projecting external rib, the rib diameter being such that it engages the tube inner surface to retain the plug in the tube. The rib can have an angled outer surface which diverges radially towards the tube end and terminates in a relatively sharp edge. The plug can then slide relatively easily into the tube but will require a significant pulling force to remove it from the tube. The plug can have a radially extending outer flange at its end to abut the edge of the sheet at the end of the tube.

The plug can be inserted into the tube end after rolling or folding of the sheet, alternatively the sheet may be rolled around a pair of suitably positioned end plugs which act as a spindle.

DETAILED DESCRIPTION OF THE INVENTION

A device according to one embodiment of the invention will now be described by way of example with reference to the accompanying drawings in which.

Figure 2:
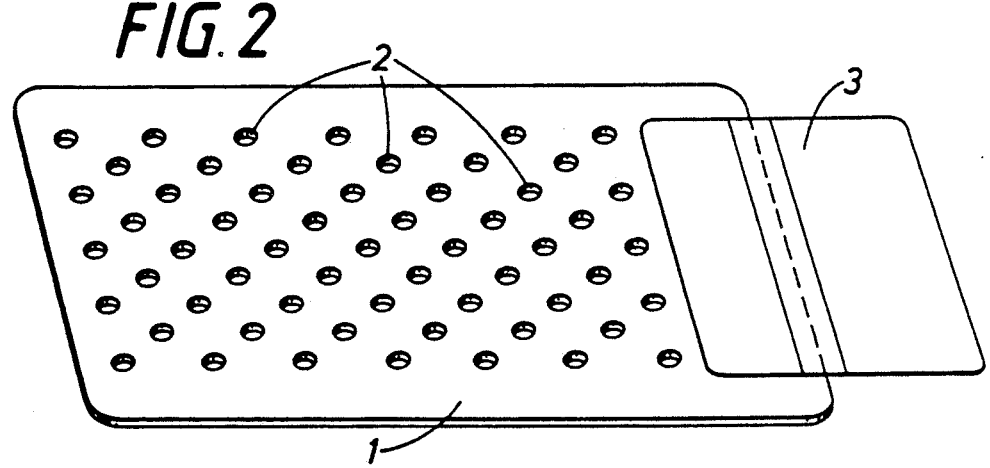
FIG. 2 shows a trilaminate sheet to be rolled up to form the device of FIG. 1.

The sheet 1 shown in FIG. 2 is a trilaminate sheet of the kind described in EP 0153070. It comprises a central resilient core sheet of ethylene vinyl acetate polymer (EVA) which is impregnated with morantel tartrate. This core sheet is coated on its upper and lower surfaces, but not its edges, with surface layers of pure EVA. The sheet is provided with a pattern of holes, two of which are punched through the trilaminate. Typical dimensions of the sheet are about 21 cm length, about 9.5 cm width and an overall thickness of 2.15 mm made up of the core having a thickness of 1.91 mm and the surface layers each of 0.12 mm thickness. The holes may be of 2.7 mm diameter.

The EVA of the core provides a matrix containing the morantel tartrate. The weight of morantel tartrate is approximately equal to the weight of EVA in the core and the device shown in the drawing contains about 11.8 g of morantel as the tartrate salt.

When the trilaminate sheet is present in the rumen of an animal the rumen fluids make contact with the core at the edges of the sheet and in the holes, but not over the main surface of the core which is protected by the EVA coating which acts as a barrier layer. The morantel tartrate is then slowly released into the rumen through the edges of the sheet and the holes, the rate of release depending on the number of holes. The rate of release of morantel tartrate into the rumen is substantially uniform and may be complete after a period of 90 days in the rumen. The trilaminate sheet remains substantially intact during release of the morantel tartrate and then gradually disintegrates within the rumen.

Figure 1:
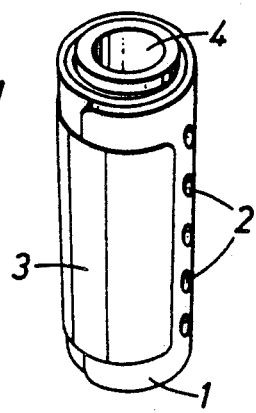
FIG. 1 shows the device in the rolled-up condition for administration to ruminant animals.
Figure 3:
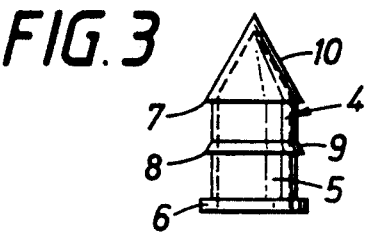
FIG. 3 shows an end plug for the device of FIG. 1.

In order to allow administration to the animal the trilaminate sheet is rolled into a cylindrical configuration as shown in FIG. 1 and is retained in this configuration by a sheet (3) of adhesive regenerated cellulose film which surrounds the cylinder sides completely and prevents the sheet unrolling until the sheet enters the rumen. The cylinder has an outer diameter of about 2.53 cm and may be administered to the animal in known manner by use of a balling gun. Once in the rumen, the cellulose film disintegrates and the trilaminate sheet unrolls under the effect of its resilience and remains in the rumen. Both ends of the cylinder are closed by circular hollow plugs (4), one of which is shown in FIG. 3. The plugs are formed of a physiologically harmless plastics material such as polyethylene and comprise a pointed cylindrical body (5) having a flange (6) at its outer end and a pair of circumstantial ribs (7) and (8) having angled outer surfaces (9) and (10) which diverge radially outwardly towards the flanged outer end of the plug. The diameter of the plug body is such that it may fit tightly into the tube formed by the rolled-up sheet (1); in the embodiment shown the body (5) has an outer diameter of 9.89 mm and the maximum diameter of the ribs is 13.70 mm. The materials of the plug and the sheet both have a certain degree of resilience and the diverging shape of the ribs is such that the plug may readily be inserted in the tube formed by the sheet, the flange (6) abutting the end of the rolled tube, and after insertion the plug is retained in the tube by the ribs (7) and (8).

As the plugs are firmly retained in the tube, they remain in place when the device is administered to an animal and passes through the oesophagus to the rumen. As the device uncoils in the rumen the plugs are released and become detached from the sheet (1) so that they do not interfere with the action of the sheet in discharging morantel tartrate in the rumen. The plugs are eventually discharged from the rumen, together with the remains of the disintegrated sheet, by natural processes. It has been found that when the device is administered to calves, the incidence of impaction in the oesophagus is substantially zero.

We claim:

1. A device for oral administration of a medicament to a ruminant animal comprising a trilaminate sheet, said sheet including a core sheet coated on the upper and lower surfaces, but not the edges, with an inert plastic barrier layer, said trilaminate sheet provided with holes and impregnated with the medicament and said sheet capable of slow release of the medicament within the rumen, the sheet being rolled or folded into a tube configuration and constrained in that configuration by an adhesive regenerated cellulose film, characterized in that the ends of the tube formed by the sheet are provided with closing means comprising physiologically acceptable plastic plugs, said closing means allowing said unrolling or unfolding of the sheet in the rumen and said closing means keeping the tube ends closed during administration of the device to the animal and passage thereof into the rumen.

2. A device according to claim 1, wherein said plugs extending into the ends of the tube and engaging the inner surface thereof.

3. A device according to claim 2, in which the plugs engage said inner surface by an interference fit.

4. A device according to claim 3, in which the plugs have a cylindrical body portion provided with at least one radially projecting external rib, the rib diameter being such that the rib engages the tube inner surface to retain the plug in the tube.

5. A device according to claim 4, in which the rib has an angled outer surface which diverges radially towards the tube end and terminates in a relatively sharp edge.

6. A device according to any one of claims 2 to 5, in which the plug has a radially extending outer flange at its end to abut the edge of the sheet of the end of the tube.

* * * * *